United States Patent
Guerrero Rivera et al.

(10) Patent No.: US 11,813,355 B2
(45) Date of Patent: Nov. 14, 2023

(54) CURCUMIN-LOADED NANOEMULSIONS, METHOD OF MANUFACTURE, AND METHOD OF PREVENTIVE TREATMENT USING THE SAME

(71) Applicant: UNIVERSIDAD DE CHILE, Santiago (CL)

(72) Inventors: Simón Juan Guerrero Rivera, Santiago (CL); Pamela Paz Contreras Orellana, Santiago (CL); Victor Díaz García, Santiago (CL); Pablo Alberto Lara Arenas, Santiago (CL); Areli Marly Cárdenas Oyarzo, Santiago (CL); Lisette Leyton Campos, Santiago (CL); Marcelo Javier Kogan Bocian, Santiago (CL); Andrew F. G. Quest, Santiago (CL); Felipe Andrés Oyarzún Ampuero, Santiago (CL); Andrea I. Vivanco Palma, Santiago (CL); Victor Andrés Miranda Miranda, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 87 days.

(21) Appl. No.: 15/856,786

(22) Filed: Dec. 28, 2017

(65) Prior Publication Data
US 2018/0185282 A1 Jul. 5, 2018

Related U.S. Application Data

(60) Provisional application No. 62/440,476, filed on Dec. 30, 2016.

(51) Int. Cl.
| | | |
|---|---|---|
| *A61K 9/107* | (2006.01) | |
| *A61K 47/44* | (2017.01) | |
| *A61K 49/00* | (2006.01) | |
| *A61K 9/00* | (2006.01) | |
| *A61P 35/04* | (2006.01) | |
| *A61K 31/12* | (2006.01) | |
| *A61K 47/08* | (2006.01) | |
| *A61K 47/10* | (2017.01) | |
| *A61K 47/14* | (2017.01) | |
| *A61K 47/24* | (2006.01) | |

(52) U.S. Cl.
CPC .......... *A61K 9/1075* (2013.01); *A61K 9/0019* (2013.01); *A61K 31/12* (2013.01); *A61K 47/08* (2013.01); *A61K 47/10* (2013.01); *A61K 47/14* (2013.01); *A61K 47/24* (2013.01); *A61K 47/44* (2013.01); *A61K 49/0021* (2013.01); *A61K 49/0078* (2013.01); *A61P 35/04* (2018.01)

(58) Field of Classification Search
CPC ........ A61K 9/107; A61K 31/12; A61K 47/14; A61K 47/24; A61K 47/08; A61K 47/10; A61K 49/00; A61K 9/1075; A61K 9/0019; A61K 47/44; A61K 49/0021; A61K 49/0078; A61K 9/19; A61P 35/04
See application file for complete search history.

(56) References Cited

U.S. PATENT DOCUMENTS

| | | | | |
|---|---|---|---|---|
| 8,835,509 | B2 * | 9/2014 | Kohli | A61K 31/12 |
| | | | | 424/455 |
| 2011/0206739 | A1 * | 8/2011 | Nicolosi | A61K 38/28 |
| | | | | 514/729 |
| 2016/0354390 | A1 * | 12/2016 | Okumu | A61K 31/635 |

FOREIGN PATENT DOCUMENTS

IN 3800MU2013 * 7/2015

OTHER PUBLICATIONS

Abbas et al. Process optimization of ultrasound-assisted curcumin nanoemulsions stabilized by OSA-modified starch, Ultrasonics Sonochemistry 21 (2014) 1265-1274. (Year: 2014).*

Raju et al., Cancer Chemopreventive and Therapeutic Effects of Diosgenin, a Food Saponin, Journal Nutrition and Cancer, vol. 61, 2008—Issue 1 (abstract). (Year: 2008).*

Plaza-Oliver et al., Design of the interface of edible nanoemulsions to modulate the bioaccessibility of neuroprotective antioxidants; International Journal of Pharmaceutics 490 (2015) 209-218, May 11, 2015 (Year: 2015).*

Liu et al., Terpene microemulsions for transdermal curcumin delivery: Effects of terpenes and cosurfactants, Colloids and Surfaces B: Biointerfaces 82 (2011) 63-70. (Year: 2011).*

Rachmawati et al. (drug Dev Ind Pharm (2015) 41(4); 560-566).*

* cited by examiner

*Primary Examiner* — Shirley V Gembeh

(74) *Attorney, Agent, or Firm* — Procopio, Cory, Hargreaves & Savitch LLP

(57) ABSTRACT

A oil-in-water curcumin nanoemulsion that includes curcumin dissolved in at least one miscible solvent and encapsulated in an oil core, wherein the oil core also comprises a stabilizer, wherein the oil core forms an organic phase which is dispersed in an aqueous solvent, and wherein the oil core is selected from a pharmaceutically acceptable oil. A method of manufacturing an oil-in-water curcumin nanoemulsion includes dissolving the curcumin in at least one miscible solvent; encapsulating the curcumin in the oil core to produce an organic phase solution; adding the stabilizer to the organic phase solution; dispersing the organic phase solution in the aqueous solvent; and evaporating the mixture. A method of preventing metastatic cancer using an oil-in-water curcumin nanoemulsion by administering an amount of the nanoemulsion topically to an area of an excised primary tumor, and monitoring any reincidence of metastatic cancer in the excised primary tumor area.

7 Claims, 10 Drawing Sheets

FIGURES 5A/5C

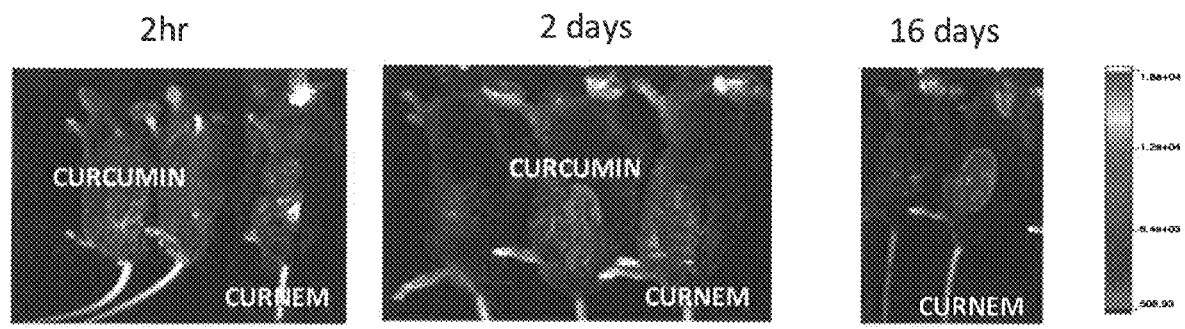
FIGURE 7D
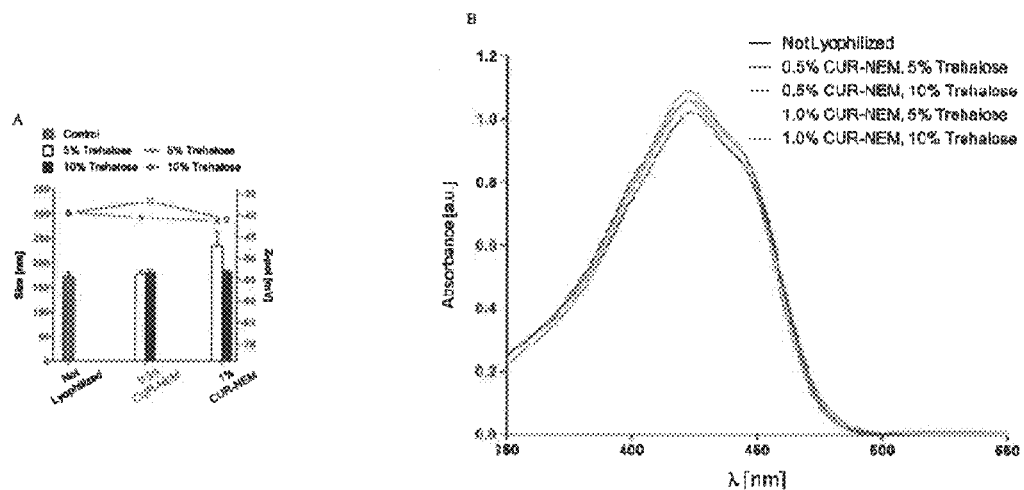
FIGURE 8A  FIGURE 8B

CURCUMIN-LOADED NANOEMULSIONS, METHOD OF MANUFACTURE, AND METHOD OF PREVENTIVE TREATMENT USING THE SAME

FIELD OF THE INVENTION

The present invention relates to compositions, their method of manufacture, and a treatment for cancer. More particularly, the present invention relates to oil-in-water curcumin nanoemulsions and their method of manufacture for preventive treatment of melanoma metastasis after post-surgical removal of primary tumors.

BACKGROUND

Skin cancer is one of the most common types of cancer and the number of cases is increasing worldwide. Three main types of skin cancer exist: (1) basal cell carcinoma; (2) squamous cell carcinoma; and (3) melanoma, which affect melanocytes. Among them, melanoma is the most lethal cancer type—which is characterized by rapid progression and high resistance to chemotherapy.

Additionally, high degrees of invasiveness and metastasis represent the major factors that contribute to poor prognosis and define the outcome for melanoma patients. According to the World Health Organization, approximately 80% of all skin cancer-related deaths can be attributed to melanoma and long-term survival of patients with metastatic melanoma is only 5%.

Despite extensive research efforts, options for the treatment of metastatic disease, beyond invasive surgical interventions, do not exist. Until recently, only three drugs received FDA approval for the treatment of melanoma, namely dacarbazine, hydroxyurea, and interleukin-2 (IL-2). All of these drugs focus on inhibiting cancer growth, but are essentially ineffective in preventing metastasis. In the case of dacarbazine, only 15% of patients respond and only 1-2% patients survive for extended periods. In addition, and as is commonly observed for chemotherapeutic drugs, dacarbazine is toxic to normal human cells in addition to cancer cells. Thus, these treatments generate significant side effects in patients and the efficacy is limited by the doses of the drug that can be tolerated.

Animal models exist that mimic important aspects related to the progression and outcome of melanoma. For example, following surgical removal of subcutaneous melanomas in rodents, tumor reincidence (at the same site) and metastasis to the lung can be evaluated in the same animal. Both tumor reincidence and metastasis represent important criteria necessary to evaluate preclinical efficacy of surgical and/or pharmacological treatments and to predict survival times.

Curcumin (1,7-bis(4-hydroxy-3methoxyphenyl)-1,6-heptadien-3,5-dione) is the main bioactive component of turmeric. Several research groups have shown that curcumin possesses a wide range of anti-tumor properties, likely due to its ability to induce cancer cell death and apoptosis, as well as to inhibit cancer-related angiogenesis. Previous studies have shown that curcumin is effective against metastasis, as evidenced by a reduction in the number of lung tumor nodules attributed to alterations in lysosomal integrity and inhibition of proteolysis to reduce cell invasion. Additionally, curcumin has also been shown to display a very favorable safety profile in humans, which includes no dose-limiting toxicity up to 12/g/day). Several phase I and phase II clinical trials have demonstrated promising effects of oral curcumin administration in patients with colorectal neoplasia, advanced pancreatic and breast cancer—either with or without additional chemotherapy. More specifically, curcumin displays anti-melanoma efficiency both in vitro and in vivo.

Despite the great therapeutic potential of curcumin in a variety of cancers (including melanoma), its clinical application has been strongly hindered due to a number of limiting characteristics including: rapid metabolism, poor water solubility, instability at neutral pH and upon exposure to light and/or oxygen, and poor uptake by tissues. The above characteristics drastically limit the potential utility of curcumin in cancer treatments.

Due to poor water solubility and absorption characteristics, those of ordinary skill dissolve curcumin in organic solvents like dimethylsulfoxide (DMSO) prior to in vitro and in vivo evaluation. Although DMSO helps to solubilize curcumin and to improve availability, its use as a vehicle is controversial. A variety of studies have demonstrated that DMSO induces, in vitro and in vivo, severe cell damage due to effects on cell metabolism and membrane integrity—with many toxic side effects. The cytotoxicity results of these types of nanoemulsions are known for other cell lines. S. Anuchapreeda, Y. Fukumori, S. Okonogi and H. ichikawa, Preparation of Lipid Nanoemulsions Incorporating Curcumin for Cancer Therapty, J. Nanotechnol. 2012; 2012:11 evaluated the cytotoxic effects of their curcumin-loaded nanoemulsions at different concentrations, in cell lines B16F10 (murine melanoma), K562 (erythroleukemia), Molt4 (human acute lymphoblastic leukemia), U937 (monoblastic leukemia), and HL-60 (promyelocytic leukemia) during a 48-hour exposure period. The inventors have previously described that nanoemulsions with curcumin (solubilized in DMSO) are able to inhibit cell growth in all of the cell lines studied, and obtained the $CI_{50}$ values of approximately 22.2, 53.7, 30.3, 35.8, and 23.5 µM, respectively, for loaded nanoemulsions, but whereas the $CI_{50}$ obtained by means of a treatment with free curcumin (solubilized in DMSO) were approximately 3.5, 38.7, 14.4, 30.1, and 15.7 µM, respectively, keeping the tendency that the curcumin solubilized in DMSO is more cytotoxic than an encapsulated curcumin. The effects of curcumin on HeLa cell line using other carriers are also known. For example, Das, L and M. Vinayak, Long term effect of curcumin in regulation of glycolytic pathway and angiogenesis via modulation of stress activated genes in prevention of cancer Plos One, 2014, 9(6): p.e99583 developed nanoparticles composed of alginate, chitosan and pluronic, and evaluated their effectiveness on HeLa, describing an $CI_{50}$ of 13.28 and 14.34 µM for free and encapsulated curcumin, respectively.

Nanovehiculization in oil-in-water (O/W) carriers offers important opportunities for the therapeutic application of lipophilic molecules like curcumin. This carrier renders such molecules soluble in the oil core (thus being able to interact with biological receptors), while being dispersible in aqueous media allowing direct administration in biological fluids (blood, soft tissues, gastrointestinal tract, etc.). Thus, a major advantage of this carrier is that it avoids the administration of organic solvents with topical/systemic toxicity. Additionally, enclosure of curcumin in the lipid core of such nanovehicles protects the molecule against conditions and factors present in the biological environment (neutral pH, oxygen, enzymes and free radicals, etc.) known to destabilize curcumin; by doing so, the carrier is significantly improving the biological effects of curcumin.

Therefore, the need remains to efficiently encapsulate curcumin in the oil core of O/W nanoemulsions that are safe, readily dispersible in biological media, and avoid toxic solvents for the administration of and inhibition of the proliferation, migration and invasion of melanoma cells to prevent tumor reincidence and metastasis in post-surgical cancer patients.

BRIEF SUMMARY OF THE INVENTION

In one aspect of the invention, an oil-in-water curcumin nanoemulsion includes curcumin dissolved in at least one miscible solvent and encapsulated in an oil core, wherein the oil core also comprises a stabilizer, wherein the oil core forms an organic phase which is dispersed in an aqueous solvent, and wherein the oil core is selected from a pharmaceutically acceptable oil. The weight of the curcumin is from about 10 mg to about 20 mg per 100 ml of the at least one miscible solvent, and particularly, the weight of the curcumin is from about 12 mg to about 15 mg per 100 ml of the at least one miscible solvent. The pharmaceutically acceptable oil is selected from the group consisting of soybean oil, ethyl oleate, ethyl butyrate, ethyl caprylate, Miglyol 812, mineral oil, liquid paraffin, medium-chain triglyceride oil, grapeseed oil, and combinations thereof. More particularly, the pharmaceutically acceptable oil is Miglyol 812. The amount of the pharmaceutically acceptable oil added is about 400 µl to about 800 µl per 100 ml of the aqueous solvent, and more particularly, the amount of pharmaceutically acceptable oil added is about 500 µl to about 700 µl per 100 ml of the aqueous solvent. The stabilizer in the oil core is selected from the group consisting of an ionic surfactant, Epikuron 145 V, lecithin, agar, carrageenan, gellan, gelatin, guar gum, sodium alginate, xanthan gum, and combinations thereof. More particularly, the stabilizer is Epikuron 145 V. The weight of the stabilizer added is about 100 mg to about 500 mg per 100 ml of the at least one miscible solvent, and more particularly, the weight of the stabilizer added is about 200 mg to about 400 mg per 100 ml of the at least one miscible solvent. The aqueous solvent may be water. The at least one miscible solvent is selected from the group consisting of acetone, ethanol, and combinations thereof. More particularly, the at least one miscible solvent is a combination of acetone and ethanol.

In another aspect of the invention, a method of manufacturing an oil-in-water curcumin nanoemulsion includes dissolving the curcumin in at least one miscible solvent; encapsulating the curcumin in the oil core to produce an organic phase solution; adding the stabilizer to the organic phase solution; dispersing the organic phase solution in the aqueous solvent; and evaporating the mixture until a volume of about 1 ml to about 10 ml remains. The evaporation of the mixture may occur under a vacuum. More particularly, the method may further include lyophilization of the mixture into a dry powder.

In yet another aspect of the invention, a method of preventing metastatic cancer using the oil-in-water curcumin nanoemulsion includes administering an amount of the nanoemulsion topically to an area of an excised primary tumor, and monitoring any reincidence of metastatic cancer in the excised primary tumor area.

Numerous other features and advantages of the present invention will be readily apparent to those of ordinary skill in the art upon reading of the following detailed description of presently preferred, but nonetheless illustrative, embodiments of the present invention when taken in conjunction with the accompanying figures. In this respect, before explaining embodiments of the invention in detail, it is to be understood that the invention is not limited in its application to the details of construction and to the arrangements of the components set forth in the following description or illustrated in the figures. The invention is capable of other embodiments and of being practiced and carried out in various ways. Also, it is to be understood that the phraseology and terminology employed herein are for the purpose of description and should not be regarded as limiting.

Before undertaking the detailed description of the invention below, it may be advantageous to set forth definitions of certain words and phrases used throughout this patent document. Throughout this specification, unless the context requires otherwise, the word "comprise" or variations such as "comprises" or "comprising" or the term "includes" or variations, thereof, or the term "having" or variations, thereof will be understood to imply the inclusion of a stated element or integer or group of elements or integers but not the exclusion of any other element or integer or group of elements or integers. Furthermore, a person skilled in the art of reading claimed inventions should understand that "a" and "an" each generally denotes "at least one," but does not exclude a plurality unless the contextual use dictates otherwise. And that the term "or" denotes "at least one of the items," but does not exclude a plurality of items of the list.

Those skilled in the art will appreciate that the invention described herein is susceptible to variations and modifications other than those specifically described. It is to be understood that the invention includes all such variations and modification which fall within its spirit and scope.

BRIEF DESCRIPTION OF THE FIGURES (NON-LIMITING EMBODIMENTS OF THE DISCLOSURE)

The invention will be better understood and aspects other than those set forth above will become apparent when consideration is given to the following description thereof. Such description makes reference to the annexed figures, wherein:

FIG. 5A is a graph of the flow cytometry accumulation data of cultured metastatic B16F10 murine melanoma cells after treatment with and according to at least one embodiment of the invention.

FIG. 5O is a chart of co-localization accumulation data of cultured metastatic B16F10 murine melanoma cells after treatment with and according to at least one embodiment of the invention.

FIG. 7D is a series of is a scanned transmission electron microscope (STEM) images of the persistent fluorescence of the curcumin signal after excision and treatment with and according to at least one embodiment of the invention.

FIG. 8A is a chart of the particle size and zeta potential related to the stability before and after lyophilization of at least one embodiment of the invention.

FIG. 8B is a UV-vis spectrum graph before and after lyophilization of at least one embodiment of the invention.

Figure 1:
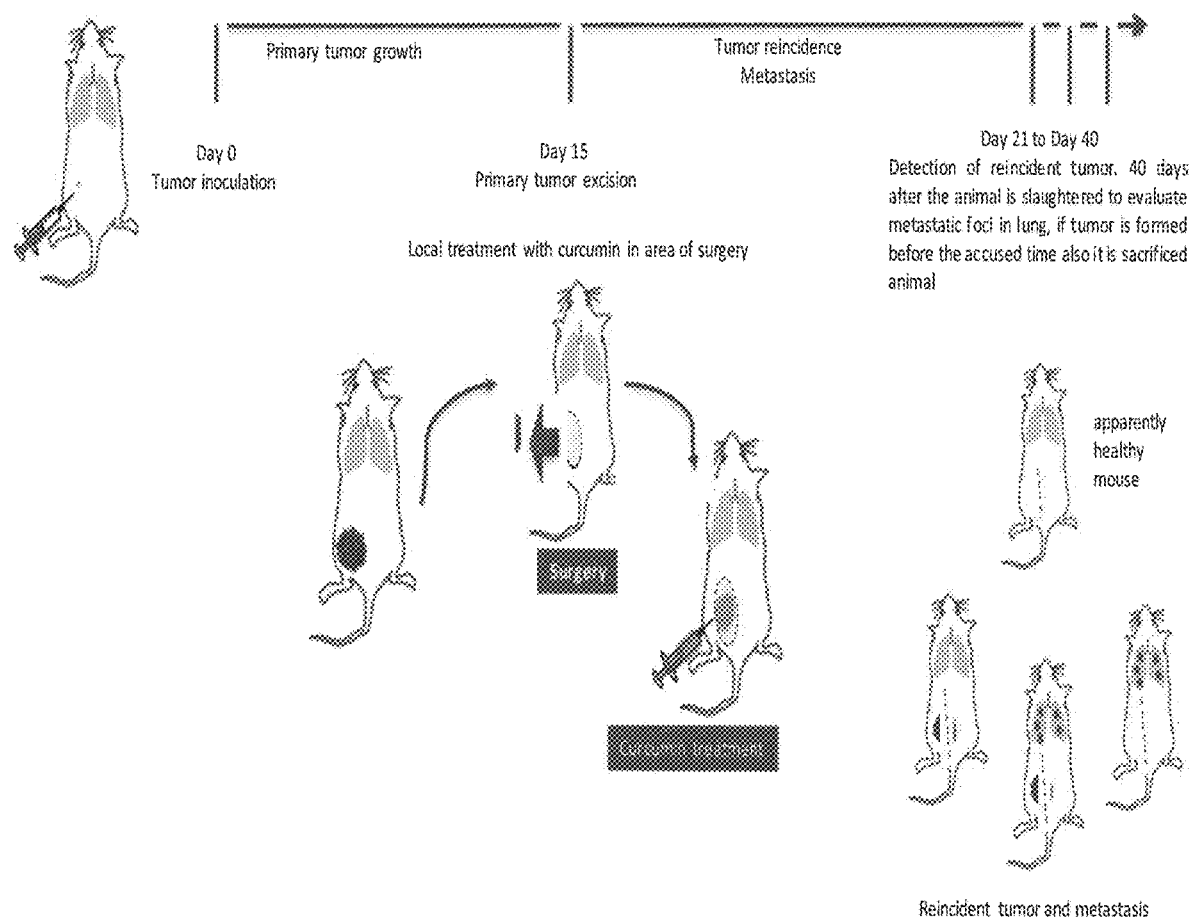
FIG. 1 is a schematic diagram of a general experimental design according to Example 1 according to at least one embodiment of the invention.

The file of this patent contains at least one drawing executed in color. Copies of this patent with color drawing(s) will be provided by the Office upon request and payment of the necessary fee.

DETAILED DESCRIPTION

Hereinafter, an oil-in-water curcumin nanoemulsion, a method of manufacture of the oil-in-water curcumin nanoemulsion, and a method of preventive treatment are described. The development and the in vitro/in vivo evaluation of a novel anti-melanoma oil-in-water curcumin nanoemulsion are also described. The nanoemulsion is composed of a lipid core containing curcumin and stabilized by an ionic surfactant. The advantages of this invention include its simplicity (minimum amount of components and easy to produce), bio acceptability, and efficacy (demonstrated anti-tumor activity and metastasis inhibition).

The oil-in-water curcumin nanoemulsions contain round shaped, homogeneous in size curcumin particles around 200 nm (PDI≥0.2) with negative zeta potential and a curcumin encapsulation efficiency of 80%. In vitro assays show that this nanoemulsion is safe in non-cancerous human cells (HEK-293T) and preferentially active in murine melanoma cell (B16F10). The oil-in-water curcumin nanoemulsion increases intracellular curcumin accumulation and is demonstrated in vitro to increase reactive oxygen species (ROS) levels while preventing migration and invasion of melanoma cells. In vivo studies demonstrate that a single dose of the oil-in-water curcumin, applied topically in the area of an extirpated primary tumor, is sufficient to prevent reincident melanoma growth and lung metastasis.

Additionally, these nanoemulsions are nanocarriers readily dispersible in biological media thereby permitting direct administration of curcumin. The ability of nanocarriers loaded with curcumin to inhibit the proliferation, migration and invasion of melanoma cells was evaluated in vitro. The safety and biological selectivity of the nanoemulsion was also evaluated in vitro in human embryonic kidney (HEK293T) cells. The ability of these nanoemulsions to improve curcumin accumulation as well as ROS formation in melanoma cells was determined. Finally, these oil-in-water curcumin nanoemulsions were tested in a preclinical animal model of melanoma, whereby tumor reincidence and metastasis to the lung were evaluated following surgical removal of the initial tumor and applying topically the nanoemulsion. The in vitro results showed that such nanoemulsions were safe and effective at inhibiting proliferation, migration and invasion of melanoma cells while increasing ROS levels and promoting intracellular accumulation of curcumin. Importantly, a single dose was determined to be remarkably effective at preventing completely tumor reincidence and lung metastasis in vivo.

The nanoemulsion can be converted to a dry powder by lyophilization and is shown, upon reconstitution, to maintain the size and zeta potential of the colloid as well as the UV-vis spectrum of curcumin. Considering the remarkable biocompatibility of the oil-in-water curcumin nanoemulsion and that the clinically indicated first line of defense against melanomas, and indeed a variety of malignant tumors, is extirpation, the nanoemulsion is an ideal agent to be applied in patients following cancer surgery, to prevent tumor reincidence and metastasis.

One embodiment of the invention is an oil-in-water curcumin nanoemulsion comprising curcumin dissolved in at least one miscible solvent and encapsulated in an oil core, wherein the oil core also comprises a stabilizer, wherein the oil core forms an organic phase which is dispersed in an aqueous solvent, and wherein the oil core is selected from a pharmaceutically acceptable oil.

A. Curcumin

Curcumin (theracurmin, turmeric extract, curry extract) is fat soluble and useful in the oil-in-water nanoemulsion for the anti-tumor properties. Curcumin is known to inhibit cancer cell growth (including melanoma cells and to some extent metastasis) with minimal side effects in normal tissues. The weight of the curcumin should be determined in relation to the total mass/weight percentage of the nanoemulsion, as it is not effectively absorbed to observe the anti-tumor properties in low concentrations, whereas high concentrations may cause DNA damage and suppress the immune system at high concentrations. In one embodiment of the oil-in-water curcumin nanoemulsion, the weight of the curcumin is from about 10 mg to about 20 mg per 100 ml of the at least one miscible solvent. In a more preferred embodiment of the oil-in-water curcumin nanoemulsion, the weight of the curcumin is from about 12 mg to about 15 mg per 100 ml of the at least one miscible solvent.

B. Oil Core

The oil core is added to an aqueous solvent to create an oil-in-water curcumin nanoemulsion. Any pharmaceutically acceptable oil may be used to create the oil core of the oil-in-water curcumin nanoemulsion. This includes but is not limited to soybean oil, ethyl oleate, ethyl butyrate, ethyl caprylate, Miglyol 812, mineral oil, liquid paraffin, medium-chain triglyceride oil, grapeseed oil, and combinations thereof. A neutral oil is preferred as it has a low or medium viscosity and prevents further reactivity with the curcumin between any additional reagents in an organic phase. In one preferred embodiment of the invention, the neutral oil is Miglyol 812. The amount of the pharmaceutically acceptable oil added to create the oil-in-water curcumin nanoemulsion should be enough to overcome the interfacial tension between the two phases as the nanoemulsion is mixed. In one embodiment of the oil-in-water curcumin nanoemulsion, the amount of pharmaceutically acceptable oil added is about 400 µl to about 800 µl per 100 ml of the aqueous solvent. In a more preferred embodiment of the oil-in-water curcumin nanoemulsion, the amount of pharmaceutically acceptable oil added is about 500 µl to about 700 µl per 100 ml of the aqueous solvent.

C. Stabilizer

The stabilizer is a molecule that has a hydrophobic (fat soluble) portion and a hydrophilic (water soluble) portion to act as an emulsifier and aid in overcoming the interfacial tension between the oil and the aqueous solvent phases of the nanoemulsion. The stabilizer also aids in decreasing the coalescence of dispersed droplets. The stabilizer can be of any type commonly known, including but not limited to an ionic surfactant, Epikuron 145 V, lecithin, agar, carrageenan, gellan, gelatin, guar gum, sodium alginate, xanthan gum, and combinations thereof. In a preferred embodiment of the oil-in-water curcumin nanoemulsion, the stabilizer is Epikuron 145 V. The weight of the stabilizer added to curcumin dissolved in the at least one miscible solvent is about 100 mg to about 500 mg per 100 ml of the at least one miscible solvent. In a preferred embodiment, the weight of the stabilizer added is about 200 mg to about 400 mg per 100 ml of the at least one miscible solvent.

D. Aqueous Solvent

It is commonly known that there are two basic types of emulsions: oil-in-water (O/W) and water-in-oil (W/O). When oil and water are mixed, the resulting emulsion usually has a higher viscosity than each of the components before the emulsification process. In an embodiment of the nanoemulsion, an aqueous solvent is added to the organic phase solution. In a preferred embodiment, the aqueous solvent is water.

E. Miscible Solvent

The at least one miscible solvent that the curcumin is dissolved in is known for adding bulk to a nanoemulsion, aiding in the facilitation of the drug absorption or solubility of the curcumin by a patient while avoiding interaction with the curcumin, and provides stability to the nanoemulsion to prevent denaturation. The miscible solvent can be of any type commonly known, including but not limited to polar and nonpolar solvents, fillers (plant cellulose, dibasic calcium phosphate, lactose, sucrose, glucose, mannitol, sorbitol, calcium carbonate, magnesium stearate), binders (gelatin, cellulose, cellulose derivatives, polyvinylpyrrolidone, starch, sucrose, polyethylene glycol [PEG]), disintegrants (carboxymethyl cellulose), natural and synthetic sorbents, antiadherents, lubricants, glidants, preservatives, antioxidants, buffering agents, chelating agents, viscosity imparting agents, surface active agents, humectants, and combinations thereof. In a preferred embodiment of the oil-in-water curcumin nanoemulsion, the at least one miscible solvent is selected from acetone, ethanol, and combinations thereof. In a more preferred embodiment, the at least one miscible solvent is a combination of acetone and ethanol.

Another embodiment of the invention is a method of manufacturing an oil-in-water curcumin nanoemulsion. The curcumin-loaded nanoemulsions of this application were prepared by a simple method that involve the addition of an organic phase including curcumin to an aqueous phase (water) and then eliminating the organic solvents. Using this strategy, the nanoemulsification process is spontaneously induced, hence avoiding the necessity for energy-consuming steps.

In one embodiment of the method, the method includes dissolving the curcumin in at least one miscible solvent; encapsulating the curcumin in the oil core to produce an organic phase solution; adding the stabilizer to the organic phase solution; dispersing the organic phase solution in the aqueous solvent; and evaporating the mixture until a volume of about 1 ml to about 10 ml remains. In a preferred embodiment, the evaporation of the resulting mixture occurs by rotaevaporation. In a more preferred embodiment, the evaporation of the oil-in-water curcumin nanoemulsion occurs under a vacuum.

In another embodiment of the method, an additional step of freeze-drying (lyophilization) of the oil-in-water curcumin nanoemulsion into a dry powder may optionally occur. Freeze-drying (lyophilization) is one of the most frequent and efficient methods to maintain the properties of nanoparticulate systems during storage, while allowing an easier transport due to the lower weight of the final product (total elimination of water). Additionally, the absence of water significantly diminishes the possibility of contamination by microorganisms, which in turn decreases the quantity of preservatives that need to be used. Nevertheless, this process becomes more complex in the case of oil/water formulations due to the presence of the oil core, which is susceptible of leakage. In this instance (to prevent the collapse of oil nanocarriers), the use of cryoprotectant agents is necessary. Any biocompatible cryoprotectants commonly known can be used, including but not limited to sugars, starches, and polyols. In a preferred embodiment of this method, the cryoprotectant is trehalose because it is less hygroscopic and possesses a higher glass transition temperature.

Another embodiment of the invention is a method of preventing metastatic cancer using the oil-in-water curcumin nanoemulsion comprising administering an amount of the nanoemulsion topically to an area of an excised primary tumor, and monitoring any reincidence of metastatic cancer in the excised primary tumor area.

Referring now to FIG. 1, a general scheme summarizing the procedures in animal experiments, including the time course of tumor formation, the surgery, the treatment post-surgery with a curcumin-loaded nanoemulsion and finally evaluation of reincident tumor growth and metastasis using an oil-in-water curcumin nanoemulsion is shown according to the following non-limiting testing examples. The time course includes tumor inoculation at day 0, primary tumor excision by surgery and local treatment with a curcumin-loaded nanoemulsion in the area of surgery at day 15, and if there is any reincident tumor growth and metastasis post-surgery, there is detection of reincident tumor(s) from day 21-40 in the test animals by examination and evaluation of a subject post-mortem. Specifically, in mice, metastatic foci in the lung was evaluated post-mortem at day 40 after surgery and curcumin treatment.

Examples

Preparation of Curcumin Loaded Nanoemulsions (CUR-NEM):

An oil-in-water curcumin nanoemulsion (NEM) was prepared following a solvent displacement method, which comprised adding 125 µl of Miglyol to an organic phase with 30 mg of Epikuron and 2.76 mg curcumin (CUR) dissolved in 0.5 mL of ethanol and 9.5 mL of acetone. This organic phase was then mixed with 20 mL of water. NEM formation was instantaneous, as evidenced by a milky appearance of the mixture. The above NEM formation was evaporated under vacuum in a rotavap until a volume of 5 mL remained. The final concentration of CUR in the NEM was 1500 μm.

Table 1 summarizes the characteristics of blank NEM and those obtained when CUR was included in the oil-in-water nanoemulsion (CUR-NEM). Observations include nanocarriers in the range of 195-217 nm and showing low polydispersity values (≥0.2), which is indicative of homogeneous populations of nanosystems. The CUR-NEM showed negative zeta potential (−30 to −36 mV) which is attributed to the presence of Epikuron that comprise a mixture of zwitterionic phospholipids, anionic fatty acids, and phosphatidic acid, among others. Inclusion of CUR into the nanocarriers was efficient, as to be expected given the high lipophilicity of the molecule and a high preference for the oil nuclei of the nanocarriers. Association efficiency for CUR was similar to known values by others using other lipophilic compounds.

TABLE 1

Physicochemical properties of the blank nanoemulsions (NEM) and curcumin-loaded nanoemulsions (CUR-NEM)(mean ± S.D., n☐4).

| Formulation | Size (nm) | Polydispersity index | Zeta potential (mV) | Association efficiency (%) |
|---|---|---|---|---|
| NEM | 195 ± 10 | 0.1 ± 0.1 | −36 ± 5 | — |
| CUR-NEM | 217 ± 14 | 0.2 ± 0.1 | −30 ± 3 | 81.1 ± 0.01 |

Figure 2:
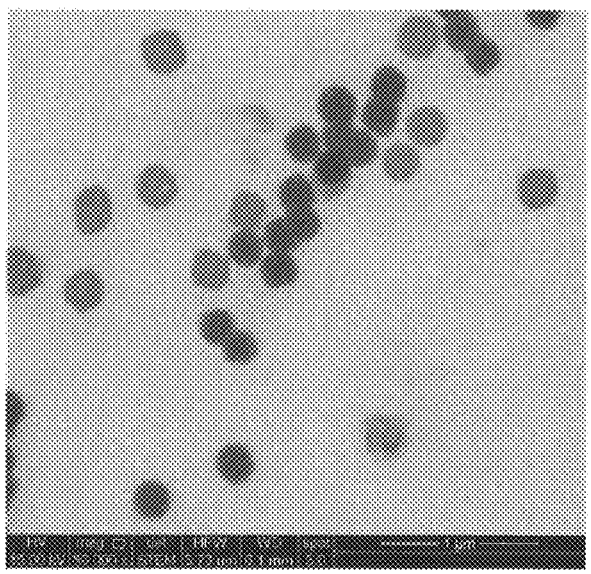
FIG. 2 is a scanning transmission electron microscopy (STEM) image of an oil-in-water curcumin nanoemulsion of according to at least one embodiment of the invention.

The morphology of such nanoemulsions was evaluated by transmission scanning electron microscopy (STEM), as shown in FIG. 2. Curcumin-loaded nanoemulsions exhibited a round particle shape. Additionally, the nanoemulsions contained curcumin particles that were homogeneous in size, coincident with results obtained by dynamic light scattering (DLS).

Physicochemical Characterization of the Oil-in-Water Curcumin Nanoemulsions:

The size and zeta potential of the colloidal systems were determined by photon correlation spectroscopy and laser Doppler anemometry, with a Zetasizer Nano-ZS (Malvern Instruments, UK). Each batch was analyzed in quadruplicate. Scanning transmission electron microscopy (STEM) images were obtained to analyze the morphology of the carriers. The samples to be analyzed were obtained by depositing one droplet (10 μl) of the oil-in-water nanoemulsion, one droplet of MilliQ-water and one droplet of phosphotungstic acid (1%) on a Parafilm® surface. A copper grid (200 mesh, covered with Formvar®, a polyvinyl formal resin produced by Monsanto Chemical Company) was then incubated with each droplet for 2 minutes. The excess liquid was eliminated with absorbent paper. The grid was allowed to dry for at least 12 h before analysis.

Encapsulation Efficiency of the Oil-in-Water Curcumin Nanoemulsions:

The encapsulation efficiency of curcumin in the oil-in-water nanoemulsions was determined by analyzing the difference between the total amount of curcumin in the nanoemulsion and the free curcumin recovered after an aliquot of the sample was isolated using Vivaspin® tubes (8500G, 20 min, MWCO 100 kD). The total amount of drug was estimated by dissolving an aliquot of non-isolated curcumin loaded nanoemulsions with acetone and measuring their absorbance at 424 nm (Lambda 25, Perkin Elmer-Germany). The amount of isolated curcumin was estimated similarly but using an aliquot of the isolated curcumin and dissolved in acetone. The standard curve of curcumin in acetone was linear ($r^2$>0.999) in the range of concentrations between 1 and 6 mg/L (molar extinction coefficient was 63291 $M^{-1}cm^{-1}$).

Cell Culture Conditions:

Metastatic B16F10 murine melanoma cells were cultured in RPMI 1640 (Roswell Park Memorial Institute) supplemented with 10% FBS, 2 mM glutamine, and antibiotics (100 U/mL penicillin and 100 μg/mL streptomycin) at 37° C. in 5% $CO_2$. Human embryonic kidney cells (HEK293T) were cultured in Dulbecco's modified Eagle medium (DMEM) high glucose and supplemented with 10% FBS, 2 mM glutamine, and antibiotics (100 U/mL penicillin and 100 μg/mL streptomycin) at 37° C. in 5% $CO_2$.

Viability Assays:

The cultured metastatic B16F10 murine melanoma cells and cultured human embryonic kidney cells (HEK293T) were seeded in 96-well plates at a density of $1\times10^4$ cells per well and incubated for 24 h in culture medium. The cells were then treated for another 24 h with 10 μL of CUR-DMSO, NEM or CUR-NEM for 24 h. 2% Sodium dodecyl sulfate (SDS) and a standard cell medium were used as positive and negative cell controls, respectively. Cell proliferation was evaluated by the MTS® assay, according to the manufacturer's (Promega, Madison, WI) instructions. Absorbance was evaluated at 490 nm removing any background absorbance (620 nm) in plate reader (Tecan Infinite 200 pro NanoQuant).

Figure 3A:
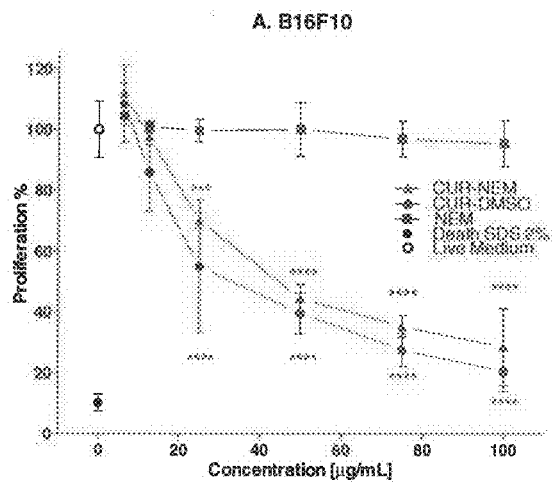
FIG. 3A is a graph of the viability assay data of metastatic murine melanoma cells (B16F10) after treatment with and according to at least one embodiment of the invention.

Cell viability was assessed in the B16F10 melanoma cells following treatment with CUR-NEM. These cells were selected because they are highly resistant to chemotherapeutic drugs, highly proliferative, and because of their elevated metastatic potential. Murine melanoma cells represent a suitable cellular model to study in C57BL/6 mice tumor appearance after subcutaneous injection, as well as reincident tumor growth and metastasis after the primary tumor has been surgically removed. As shown in FIG. 3A (the data shown is the values averaged from three independent experiments (mean±S.E.M) (P<0.01; *P<0.001; ****P<0.0001), the NEM vehicles (blank nanoemulsions) did not affect cell-viability under the conditions employed, evidencing the safety of the vehicles. Importantly, the results also indicate that CUR-NEM were as efficient in decreasing proliferation as curcumin dissolved in the organic solvent DMSO ($IC_{50}$=46±5.8 μg/mL and 34.8±7.5 μg/mL, respectively). However, as it is well documented that DMSO is toxic to cells, any strategy to promote DMSO replacement is highly desirable.

Figure 3B:
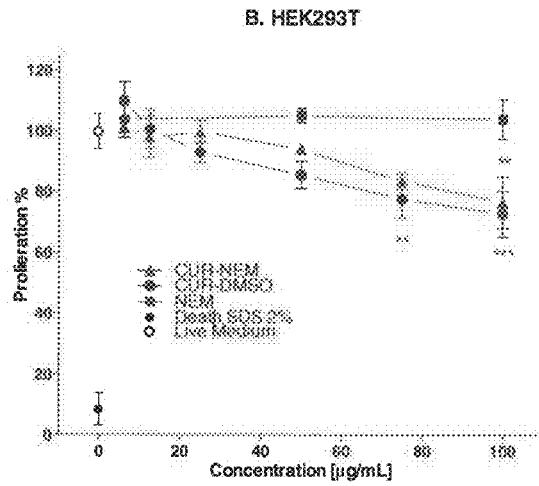
FIG. 3B is a graph of the viability assay data of human embryonic kidney cells (HEK293T) after treatment with and according to at least one embodiment of the invention.

Cell viability was also evaluated following treatment of the non-cancerous cell line (human embryonic kidney cell line) HEK-293T. At the highest doses tested, CUR-NEM diminished viability of these cells by only about 25% as shown in FIG. 3B, while NEM did not affect this parameter—confirming the safety of the nanocarrier. The results demonstrate that CUR-NEM preferentially reduced melanoma cell viability compared with non-cancerous cells.

Figure 3C:
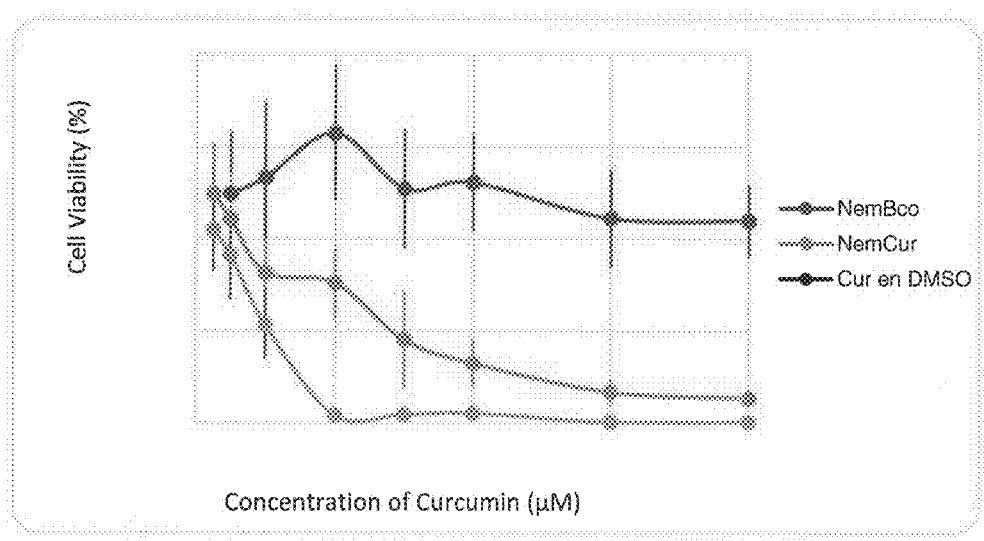
FIG. 3C is a graph of the viability assay data of human HeLa uterine cervical cancer cells after treatment with and according to at least one embodiment of the invention.
Figure 3D:
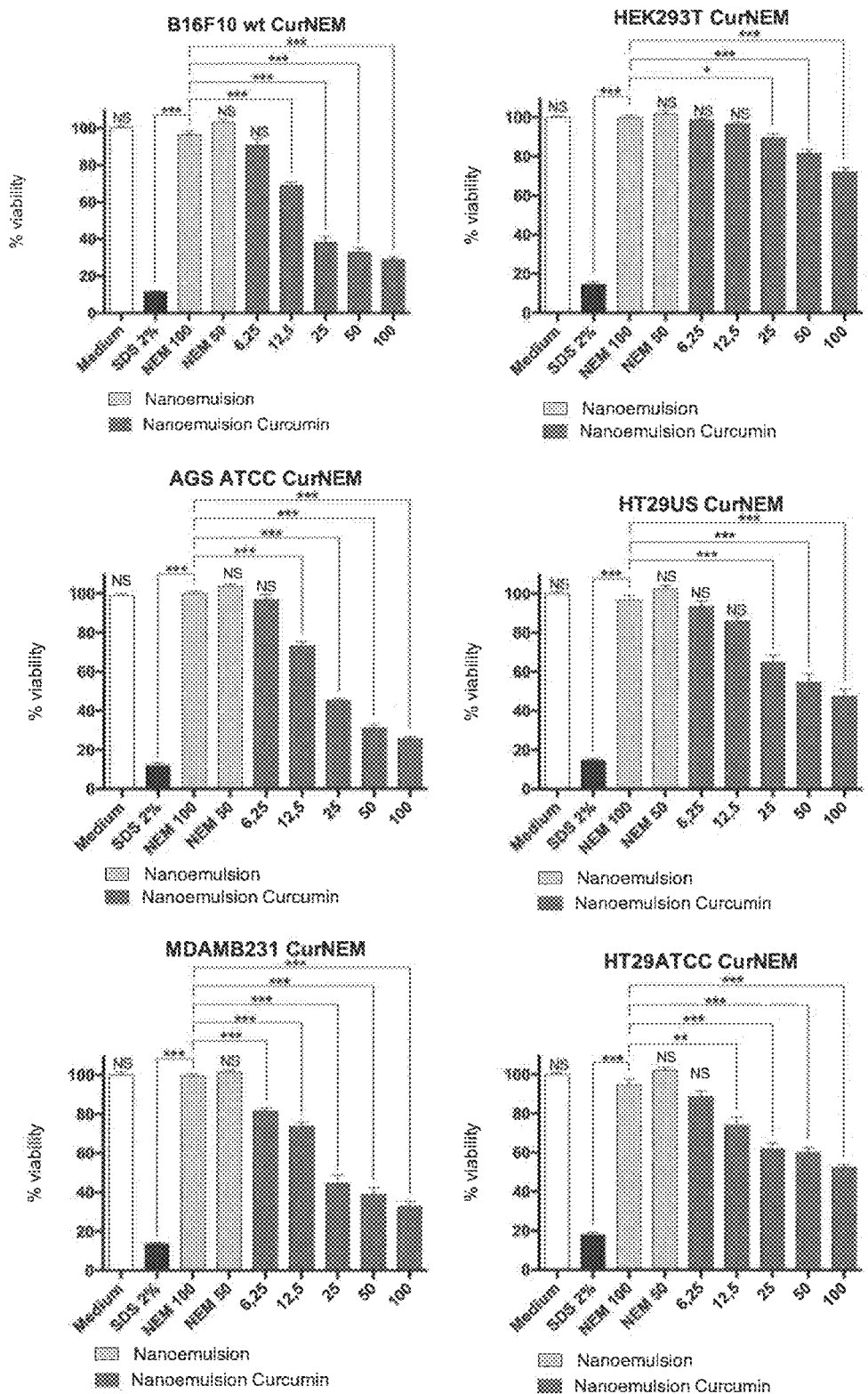
FIG. 3D is a series of graphs of the viability assay data of different cancerous and non-cancerous cell lines after treatment with and according to at least one embodiment of the invention at different concentrations.
Figure 3E:
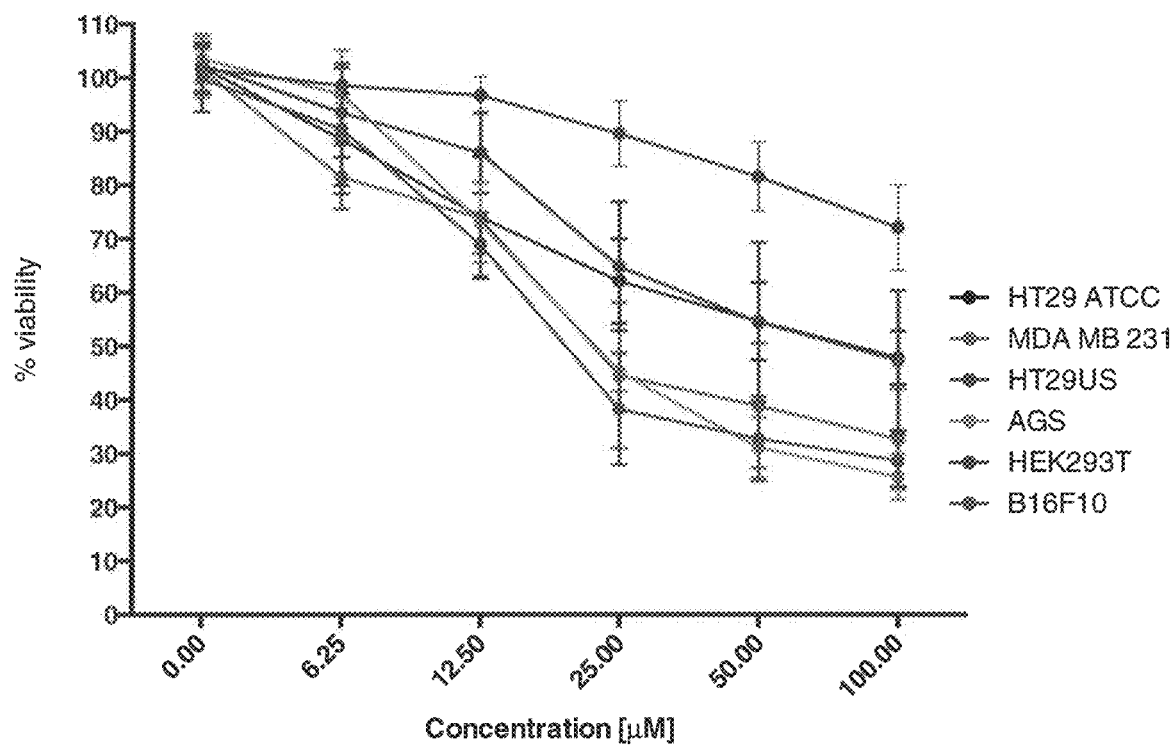
FIG. 3E is a graph summarizing the viability assay data presented in FIG. 3D.

To further determine the effect of the formulation on cell viability, the calorimetric method of tetrazolium salt reduction (CellTiter 96®) was used to establish a linear relationship between the number of metabolically active cells and the absorption intensity. To demonstrate the effective anti-carcinogenic activity of the CUR-NEM, the uterine cervical cancer cell line HeLa was used. In addition, the same concentrations of curcumin dissolved in DMSO were evaluated, in order to compare CUR-NEM and curcumin in native state, using an innocuous amount of the solvent for the culture. 2500 HeLa cells were seeded per well, in a 96-well microplate, and the cells were incubated with 100 μL of Dulbecco's Modified Eagle Medium (DMEM) culture medium enriched with 10% fetal bovine serum (FBS), at 37° C. and 5% $CO_2$. The day after seeding, the 100 μL of medium was removed, and it was replaced by 80 μL of clean culture medium. Then 20 μL of a treatment was applied, and the cells were incubated under the same temperature and $CO_2$ conditions. 24 hours after the treatment was applied, the treatment was removed, the cells were subsequently washed three (3) times with phosphate-buffered saline (PBS), and 80 μL of medium without indicator was added to the cells and 20 μL of MTS. The cells were incubated for 1 hour, and the absorbance was measured at a wavelength of 490 nm in a microplate reader. The treatments applied were CUR-NEM and CUR dissolved in dimethyl sulfoxide (DMSO). The cells were treated with concentrations of 6.25, 12.5, 25, 50, 75, 100 and 200 μM of CUR in each well of the microplate. The concentration of DMSO did not exceed 0.5% v/v. As controls, nanoemulsions without curcumin (NemBco), 0.5% v/v DMSO, sodium dodecyl sulfate (SDS) and Milli-Q water were used. Each assay was performed in triplicate. In addition, within each assay the same treatment was applied to a minimum of 5 wells. FIG. 3C shows that cytotoxicity is dependent on the concentration of curcumin, with a maximum effectiveness of 200 μM for CUR-NEM and 50 μM for the non-associated CUR, after 24-hour exposure. The $CI_{50}$ was calculated for CUR-NEM and curcumin in DMSO, being 30.5±2.3 and 61.8±18.1 μM respectively (even with NemBco not having intrinsic anticancer activity). These results also indicate that from the point 12.5 μM, the differences of CUR-NEM and CUR in DMSO are statistically significant, and when comparing the curves to life control (Milli-Q water) and NemBco, from 50 μM and 150 μM of Cur in DMSO and CUR-NEM respectively, the data is not statistically significant when compared to the SDS control.

Cell viability was also assessed in different cancer cell lines, following treatment with CUR-NEM for 24 hours. These cell lines include human gastric adenocarcinoma (AGS); colorectal adenocarcinoma (HT29); aggressive cells with elevated metastatic potential (HT29US) as compared to HT29 ATCO cells; and cells derived from a human mammary gland adenocarcinoma (MDA-MB-231). Controls corresponds to: culture medium (negative control) SDS 2% (positive control), NEM (empty nanoemulsion). (n=3, P<0.01, *P<0.001). In order to further analyze the safety of the formulations, cell viability was also evaluated following treatment of the noncancerous human embryonic kidney cell line (HEK-293T). At the highest doses tested, CUR-NEM diminished viability of these non-cancerous cells by only about 25%, while NEM (empty nanoemulsions) did not affect this parameter (in any cell line), thus confirming the safety of our nano-carrier system. These results indicate that CUR-NEM reduces viability of the different carcinoma cell lines more effectively than the HEK293T control cell line.

ROS Determination by Flow Cytometry (FACS):

The cultured metastatic B16F10 murine melanoma cells were seeded in 24-well plates at a density of $4\times10^4$ cells per well and incubated for 24 h in culture medium. Then, cells were treated with 12.5 μg/mL of CUR-NEM containing vehicles or empty vehicles (50 μL blank) for another 24 h. Once the cells and medium were recovered, ROS production was evaluated employing 2',7'-dichlorofluorescein diacetate ($H_2DCFDA$—0.1 μM) added to cells suspensions 30 min prior to completing the experiment. As a positive control, cells were incubated with freshly prepared $H_2O_2$ (0.1 mM) for 20 min at 37° C. prior to adding $H_2DCFDA$. The fluorescence of cells was analyzed by flow cytometry (Becton Dickinson, USA) at an excitation wavelength of 485 nm and at emission wavelength of 530 nm. The non-specific fluorescence of curcumin was employed as the base-line value.

Figure 4:
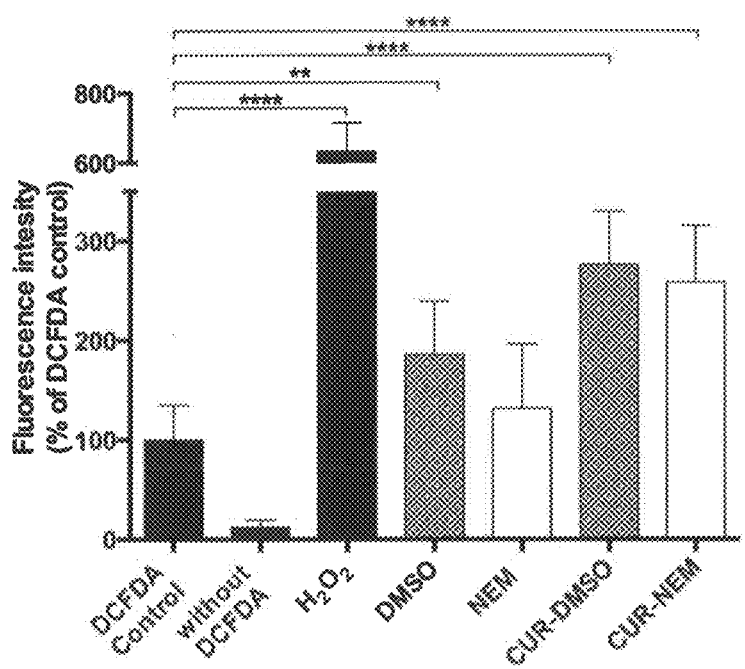
FIG. 4 is a chart of the ROS levels produced in cultured metastatic B16F10 murine melanoma cells after treatment with and according to at least one embodiment of the invention.

CUR is known to specifically increase ROS levels in cancer cells. As shown in FIG. 4, ROS levels increased in murine melanoma cells (B16F10) following administration of CUR-NEM. All formulations containing CUR (CUR-NEM and CUR-DMSO) increased ROS levels 2-fold at a dose of 12.5 μg/mL of curcumin. The DMSO solvent significantly increased the basal ROS levels, while this was not the case for the NEM (blank NEM) control. The data shown in FIG. 4 is the values averaged from three independent experiments (mean±S.E.M) (P<0.01; *P<0.001; ****P<0.0001).

Confocal Fluorescence Microscopy:

The cultured metastatic B16F10 murine melanoma cells and cultured human embryonic kidney cells (HEK293T) were seeded in 24-well plates at a density of $4\times10^4$ cells, on sterile coverslips (12 mm round coverslips glasses-Deckglässer), and grown for 24 h in complete medium. Then, cells were treated with vehicles containing 12.5 μg/mL of curcumin or empty vehicles (50 μL) for another 24 h. Cells were subsequently washed with ice-cold phosphate-buffered saline (PBS), fixed with 4% paraformaldehyde for 10 min, permeabilized with 0.1% Triton® X-100 (Sigma-Aldrich) in PBS followed by incubation with a monoclonal anti-EEA1 antibody. For detection, an Alexa Fluor 546-labeled goat anti-mouse IgG secondary antibody was used. 4',6-diamidino-2-phenylindole (DAPI) was used to stain nuclei of the cells. Coverslips were mounted on a glass slide using Fluoromount G® Mounting Medium (Southern Biotechnology Associates, USA) and sealed. Confocal images were acquired on a Zeiss LSM700 microscope (Zeiss, NY, USA) with a 63×, 1.3 water glycerin objective with a pinhole of 70 μm. The images were analyzed using the software ImageJ and Imaris.

Figure 5B:
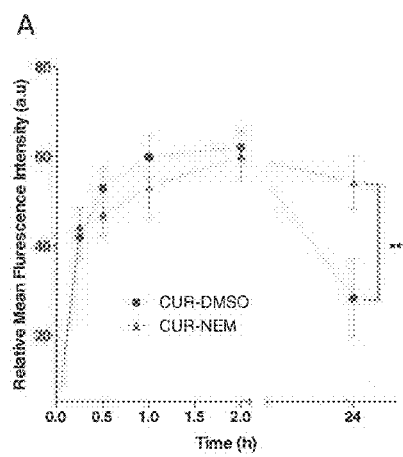
FIG. 5B are confocal images of accumulation data of cultured metastatic B16F10 murine melanoma cells after treatment with and according to at least one embodiment of the invention.
Figure 5B:
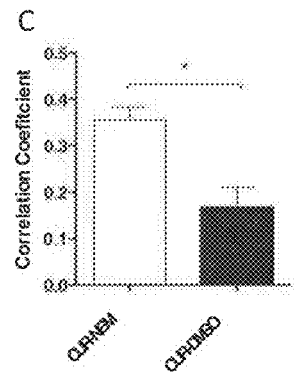
Figure 5B:
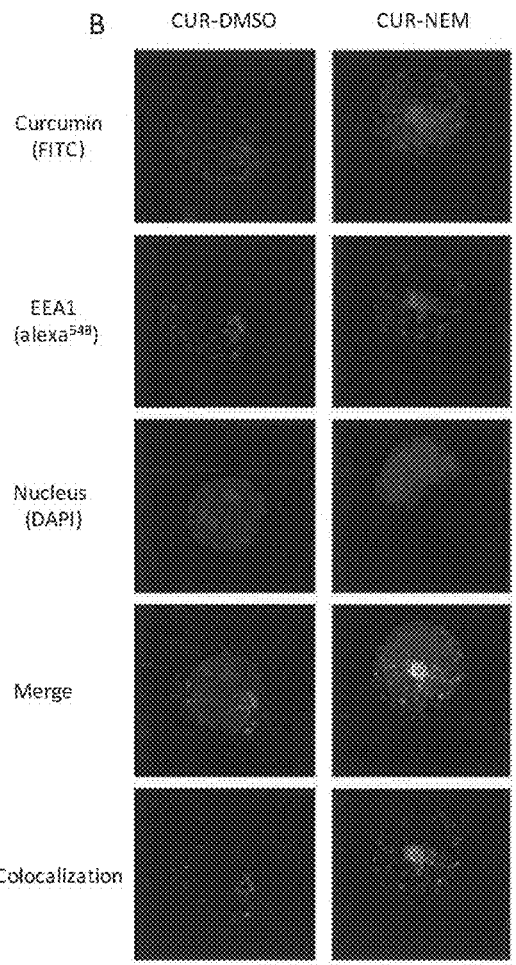

Although it is known that CUR exerts its beneficial anti-cancer effects at the intracellular level, this invention investigates whether the CUR-NEM nanoemulsion permits the interaction with and then internalization of CUR into melanoma cells. In identifying if CUR formulations (CUR-NEM and CUR-DMSO) permitted intracellular accumulation of the molecule, cells were analyzed by confocal microscopy. When added as CUR-NEM, higher levels of CUR were detectable inside cells after 24 h compared with CUR-DMSO treated cells (as shown in FIG. 5B).

Flow Cytometry:

The cultured metastatic B16F10 murine melanoma cells and cultured human embryonic kidney cells (HEK293T) were seeded in 24-well plates at a density of $4\times10^4$ cells per well and incubated for 24 h. Afterwards, cells were exposed to vehicles containing 12.5 μg/mL of curcumin or empty vehicles (50 μL) for another 24 h. Then, cells and cell medium were recovered in borosilicate glass tubes, centrifuged to remove trypsin with PBS and resuspending in FAGS buffer (PBS with 1% serum and 5 mM EDTA). The mean relative fluorescence of cell populations from the different treatment groups for different time periods (after 0.25, 0.5, 1, 2 and 24 hours) was determined and reported as mean±standard deviation of values from three independent experiments (N=3, **P<0.01).

Flow cytometry (FACS) assays indicated that CUR-NEM was rapidly and efficiently taken up by melanoma cells (detectable as early as 15 min after incubation) because CUR levels after 2 and 24 h, increased by only 36% and 22%, respectively (as shown in FIG. 5A). As can be observed, cell-associated CUR levels are similar initially for CUR-NEM and CUR-DMSO formulations (maximum after 2 h). However, while this level remained similar after 24 h following CUR-NEM incubation, the CUR values decreased by 55% in CUR-DMSO treated cells. Interestingly, co-localization (the Pearson coefficient) between CUR and the endosomal marker (EEA1 protein) was significantly higher for cells treated with the nanoemulsion (as shown in FIG. 5C), indicating that NEM may promote internalization via this pathway (N=3, *P<0.05). Importantly, in both experiments (FACS and confocal microscopy), higher levels of CUR were detectable after 24 h when administered as CUR-NEM. The results reasonably suggest that NEM formulations could significantly improving biological CUR effects in comparison with other formulations.

Transwell Migration Assays:

Prior experimental to testing, the bottom side of each insert of a Boyden Chambers system (Transwell costar, 6.5 mm diameter, 8 µm pore size) was coated with 2 µg/mL fibronectin. B16F10 cells ($5 \times 10^4$) previously treated 24 h with CUR-NEM, CUR and control, CUR-DMSO or NEM, were resuspended in serum-free medium and added to the top chamber of the insert, while serum-free medium was added to the bottom chamber. After 2 h, inserts were removed, washed, and cells that had migrated to the lower side of the inserts were stained with 0.1% crystal violet in 2% ethanol and counted in a microscope.

Matrigel Invasion Assay:

B16F10 cells ($5 \times 10^4$) were seeded, allowed to grow for 24 h, and treated with CUR-NEM, CUR and controls. Then, serum-starved cells ($2 \times 10^5$) were seeded (24 h) over 8 µm-porous inserts covered with Matrigel (Matrigel Invasion Chamber 8.0 lm; BD Biosciences Bedford, MA, USA). Inserts were fixed in cold methanol and stained with 0.5% toluidine blue in 2% $Na_2CO_3$. The membranes were mounted in Mowiol, and observed under a light microscope. At least 10 fields were evaluated (at 40× magnification) to determine the number of cells per field. The values obtained were normalized to those obtained for cells without treatment (control). Averages of values from three independent experiments are shown (mean±SEM). Statistically significant differences compared with the corresponding control group are indicated (P<0.001; **<0.0001).

Figure 6A:
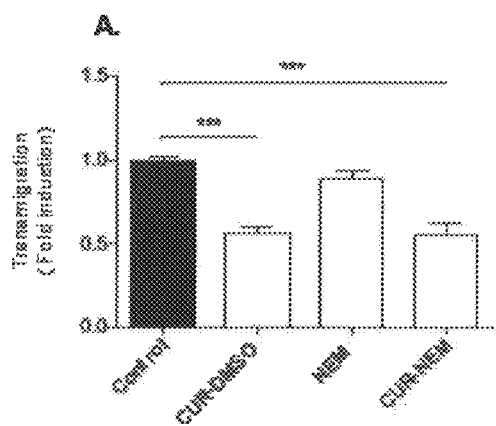
FIG. 6A is a chart of the cell migration of cultured metastatic B16F10 murine melanoma cells after treatment with and according to at least one embodiment of the invention.
Figure 6B:
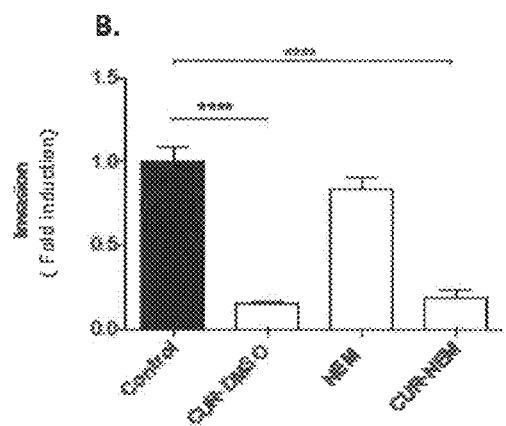
FIG. 6B is a chart of the cell invasion of cultured metastatic B16F10 murine melanoma cells after treatment with and according to at least one embodiment of the invention.

Metastasis is a complex process that is known to require migration and invasion of malignant cells. Considering that known CUR treatments have been shown to reduce migration and invasion of cancer cells, it was untested whether these beneficial characteristics were maintained in curcumin loaded nanoemulsions. As shown in FIG. 6A, migration of B16F10 cells was substantially decreased (by approximately 50%) upon cell pre-incubation for 24 hours with either 12.5 µg/ml CUR-NEM, NEM, or CUR-DMSO, while empty nanoemulsions (NEM) did not show any significant effects in this respect. Additionally, as shown in FIG. 6B, a highly significant 10-fold reduction in the invasiveness of either of the curcumin containing formulations CUR-NEM or CUR-DMSO was observed, while again no effects were detectable for NEM alone. Importantly, the nanoemulsions of the present invention are shown to maintain the beneficial effect of CUR to the same magnitude as seen for CUR-DMSO, without the necessity of employing a toxic organic solvent like DMSO. This advantageous effect strongly suggests success in vivo treatment of melanoma and potentially other kinds of metastatic cancer.

Animal in vivo Studies:

C57BL/6 mice were obtained from the Instituto de Salud Publica (Santiago, Chile) and housed in the animal facility of the Centro de Estudios Moleculares de la Celula (Instituto de Ciencias Biomedicas, Universidad de Chile). Mice between 8 and 12 weeks of age and average weight of 25 g were used for experiments. As shown in FIG. 1, a general experimental design for in vivo studies is provided.

Reincident Tumor Growth and Lung Metastasis in Animal Models

Subcutaneous tumor growth and metastasis assays in C57BL/6 mice were conducted. B16F10 cells ($3 \times 10^5$) in 100 µL physiological saline (0.9% NaCl) were injected subcutaneously into the flanks of mice. The largest perpendicular diameters of the resulting tumors were periodically measured, and tumor volumes and mass were calculated according to the following formula: $width^2 \times length \times \pi/6$. Tumors were excised by surgery after 15 days or when they reached the bioethically permitted limit of 1500 $mm^3$-2500 $mm^3$. A single dose of CUR-NEM (1500 µg/mL) and controls (NEM and physiological serum) were administered after excising the tumor to the wound zone. Volumes to be employed were calculated by correlating tumor volumes with those used for in vitro cell viability studies. Data shown (mean±S.E.M.) is averaged from results obtained with a total of N=10 mice per group (*P<0.05; **P<0.01). For example, in vitro 10 µl of CUR-NEM was administered to each well (0.3 $cm^2$ per well considering plates of 96 wells). If the area of a tumor was on average 2.5 $cm^2$ the volume of CUR-NEM added post-surgery was 83.3 µL (2.5 $cm^2$/0.3 $cm^2 \times 10$ µL). Animals were maintained for 21-30 days after surgery and then sacrificed. Reincident tumors were detected at or near the original site of tumor growth, and tumor volumes were calculated according to the previously mentioned formula. Lungs were fixed in Feketes solution and black tissues (corresponding to metastatic tumors) were separated from the rest of the lung, and weighed. Lung metastasis was expressed as black tissue mass/total lung mass in percent (%) post-fixation.

Figure 7A:
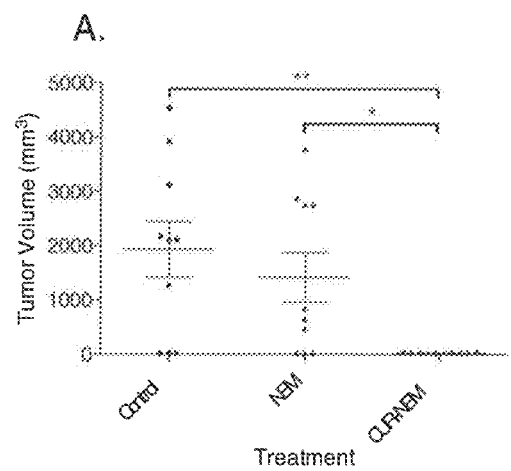
FIG. 7A is a graph of tumor reincidence data in a pre-clinical mouse model after treatment with and according to at least one embodiment of the invention.
Figure 7B:
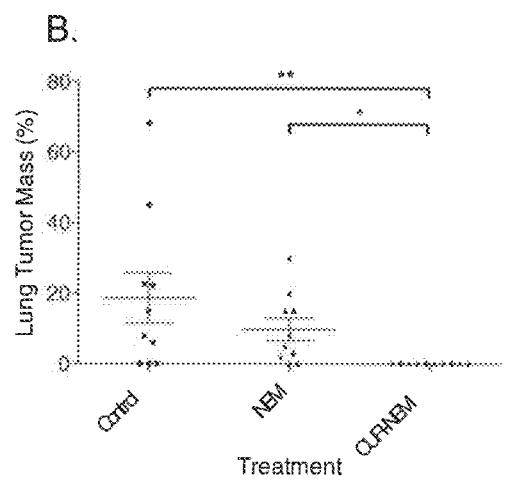
FIG. 7B is a graph of lung metastasis data in a pre-clinical mouse model after treatment with and according to at least one embodiment of the invention.

This model provides an excellent opportunity to evaluate the efficacy of pharmacological therapies mimicking the situation in humans where surgical removal of tumors is still considered the first line of defense in cancer treatment. As one of the advantages of the CUR-NEM nanoemulsions of the invention is that they deliberately avoid the use of organic solvents like DMSO to solubilize CUR, and specifically with FDA-approved excipients, the CUR-NEM should be suitable in pre-clinical/clinical therapy against melanoma reincidence and metastasis. Several reasons favor using the CUR-NEM nanoemulsions of this invention, including a) reduced melanoma growth without significantly affecting normal cells; b) increased ROS levels; c) decreased migration as well as invasion of melanoma cells; and d) more persistent accumulation of CUR in malignant cells. Administration of one dose of CUR-NEM post-surgery completely prevented tumor reincidence (as shown in FIG. 7A), while in NEM treated animals, a modest approximately 20% decline was detectable. Additionally, CUR-NEM treatment also completely abolished lung metastasis (as shown in FIG. 7B).

Figure 7C:
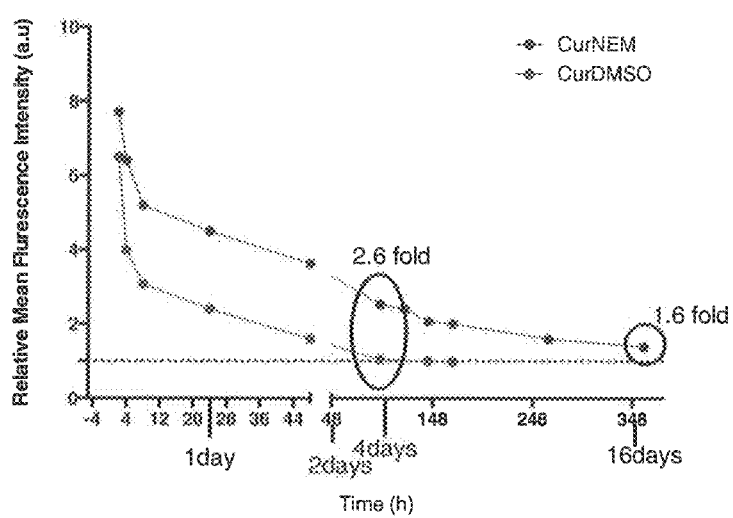
FIG. 7C is a graph of the persistent fluorescence of the curcumin signal after excision and treatment with and according to at least one embodiment of the invention.

CUR-NEM persistency after tumor excision and treatment is further shown in FIGS. 7C and 7D (curcumin fluorescence as assessed post-surgery). The results obtained were after excision of dorsally localized, sub-cutaneous tumors and treatment with CUR-NEM, and FIG. 7C compares the persistance of the curcumin signal when applied dissolved in a solvent (DMSO) or as a nanoemulsion. The signal of curcumin is maintained for a longer time in nanoemulsion than dissolved in DMSO, as shown in the fluorescence in the region of interest (ROI) values measured in vivo at different time points post-surgery (as shown in FIG. 7D) by a previously established in vitro color code.

Curcumin emits fluorescence at approximately 540 nm after excitation at 430 nm. By observing fluorescence decay over time, one may infer how long CUR-NEM remains active at the site of treatment. More extended retention may relate to a better protection of curcumin from degradation. It was observed that curcumin after CUR-NEM treatment was still detectable as fluorescence even 16 days after treatment (1.6-fold basal levels). The most significant differences compared with CUR-DMSO treatment were detected after four (4) days, when fluorescence due to CUR-NEM preparations was still 2.6-fold over basal levels, while CUR-DMSO was not detectable. Extended presence at the site of application is likely responsible for the observed inhibition of reincident tumor growth and suppression of metastasis.

Freeze-Drying Studies of Curcumin Loaded Nanoemulsions

Concentrations of NEM (0.5 and 1% w/v) loaded with CUR and the cryoprotectant trehalose (5% and 10%) were considered as the variables for a lyophilization study. 1 mL dilutions of CUR-NEM were transferred into vials of 2 mL (Eppendorf tubes) and frozen at −20° C. Samples were lyophilized (FreeZone1, Labconco Corp., USA) overnight at −53° C. and 0.1 mBar. CUR-NEM were recovered by adding 1 mL of ultrapure water to the freeze-dried powders followed by manual resuspension and such resuspended material was characterized in terms of size and zeta potential.

The UV-vis spectra of CUR from fresh nanoemuision formulations (similar to those tested in vitro and in vivo) and the freeze-dried preparations reconstituted in water were evaluated in quartz vessels and scanned at wavelengths ranging from 350 to 550 nm (Lambda 25, Perkin-Eimer-USA). For analysis, aliquots (200 μL-400 μL) of CUR-NEM, either freshly prepared or freeze dried and reconstituted in acetone (final volume 5 mL) were vigorously mixed in a vortex. The curcumin-loaded nanoemulsion formulations were then centrifuged for 30 min at 12000G (Hermle Labortechnik, Germany) and the supernatant was analyzed in the spectrophotometer.

The particle size and zeta potential of CUR-NEM upon reconstitution of the freeze-dried product as compared to a fresh formulation (Mean±S.D.; N=3) are shown (FIG. 8A). Overall, the results indicate that at relatively high concentrations of the CUR-NEM (0.5 and 1% w/v), it is possible to achieve an optimal resuspension of the dried product without altering the size and zeta potential of the original (fresh) CUR-NEM. At higher concentrations of CUR-NEM, more of the cryoprotectant trehalose is required to maintain the original characteristics of the formulation. Indeed, the spectrum of CUR is similar for fresh CUR-NEM and for the lyophilized formulations after reconstitution (as shown in FIG. 8B). These results indicate that the CUR-NEM nanoemulsions of the invention may be converted to a dry product, which will promote colloidal stability as well as the stability of the encapsulated CUR.

Acute Toxicological Assay Following Curcumin Nanoemulsion Administration

Five (5) mice underwent surgery, imitating the resective surgery of a melanoma model. The animals were all between 19.9 and 21.2 grams in weight, and approximately 6 weeks old with negative microbiological and viral patterns. A maximum volume of 300 μL of the curcumin nanoemulsion (concentration of 0.01 M of curcumin was injected into each animal. On the Six days later (post-surgery and administration), euthanasia was performed. Tissues were fixed and a complete blood analysis was made by COPD using an Epoc® system. As illustrated in Tables 2, 3 and 4, all tested parameters were normal, and thus further indicate the safety of the curcumin formulations even at doses 22 times higher than those administered in animal patients.

TABLE 2

Essential systemic metabolites measurements

| Samples | GLu mg/dL 98-152 | Lact mmol/L | Creatinine mg/dL 0.4 a 1.5 mg/dL |
|---|---|---|---|
| Mouse 1 | 100 | 2.88 | 1.58 |
| Mouse 2 | 110 | 3.23 | 1.20 |
| Mouse 3 | 118 | 2.67 | 0.36 |
| Mouse 4 | 140 | 1.88 | 0.58 |
| Mouse 5 | 157 | 1.91 | 0.56 |

TABLE 3

Measurements of metabolic chemistry in plasma

| Samples | Na 140-156 mmol/L | K 4.3-5.2 mmol/L | Ca 0.2-0.4 mmol/L | Cl 100-106 mmol/L | cTCO2 mmol/L | Hct 10-75% | cHgb 3-25 g/dL | BE(b) mmol/L |
|---|---|---|---|---|---|---|---|---|
| Mouse 1 | 139 | 4.2 | 0.33 | 103 | 13.6 | 10 | Cnc | −11.4 |
| Mouse 2 | 129 | 4.4 | 0.31 | 102 | 13.2 | 9.6 | cnc | −12.5 |
| Mouse 3 | 102 | 4.9 | 0.20 | 104 | 12.5 | 25 | 22 | −13 |
| Mouse 4 | 111 | 4.8 | 0.28 | 100 | 15 | 11 | Cnc | −11 |
| Mouse 5 | 125 | 4.7 | 0.27 | 106 | 12 | 12 | cnc | −12.0 |

TABLE 4

Measurements of plasma gases in plasma samples

| Muestra | pH 7.2-7.5 | pCO2 32-41 mmHg | pO2 mmHg | pH (T) | pCO2(T) 15-85 mmHg | pO2(T) mmHg | cHCO3— 14-24 mmol/L | BE(ecf) −30 a 30 | cSO2 0-100% |
|---|---|---|---|---|---|---|---|---|---|
| Mouse 1 | 7.2 | 43.2 | 34 | 7.21 | 31 | 21 | 21 | 9 | 76 |
| Mouse 2 | 7.02 | 32.9 | 42 | 7.12 | 28 | 20 | 15 | 3 | 75 |
| Mouse 3 | 7.1 | 38.1 | 31 | 7.23 | 29 | 10 | 17 | 10 | 62 |
| Mouse 4 | 7.1 | 53.3 | 51.8 | 7.299 | 31.5 | 22.4 | 18.2 | −10.7 | 74.7 |
| Mouse 5 | 7.2 | 42.5 | 45.6 | 7.333 | 29 | 21.0 | 21 | −12 | 70.4 |

While certain embodiments of the nanoemulsion and methods of manufacture and treatment have been described in detail with reference to the accompanying tables and figures, it should be apparent that modifications and variations thereto are possible, all of which fall within the true spirit and scope of the invention. The invention also includes all of the steps, features, compositions and compounds referred to or indicated in this specification, individually or collectively, and any and all combinations of any two or more of said steps or features.

As such, those skilled in the art will appreciate that the conception, upon which this disclosure is based may readily be utilized as a basis for other compositions, formulations, nanoemulsions, methods and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract is neither intended to define the invention of the application, which is measured by the claims, nor is it intended to be limiting as to the scope of the invention in any way.

These together with other aspects of the invention, along with the various features of novelty that characterize the invention, are pointed out with particularity in the claims annexed to and forming a part of this disclosure. For a better understanding of the invention, its operating advantages and the specific aspects attained by its uses, reference should be had to the accompanying figures and description matter in which there are illustrated preferred embodiments of the invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A topical nanoemulsion composition for topical administration, the composition comprising:
curcumin encapsulated in an oil core,
a stabilizer, and
a dispersing aqueous solvent,
wherein the oil core is selected from a pharmaceutically acceptable oil, including soybean oil, ethyl oleate, ethyl butyrate, ethyl caprylate, caprylic/capric triglyceride, mineral oil, liquid paraffin, medium-chain triglyceride oil, grapeseed oil, or combinations thereof;
the stabilizer is selected from an ionic surfactant, soy lecithin, lecithin, agar, carrageenan, gellan, gelatin, guar gum, sodium alginate, xanthan gum, or combinations thereof;
the aqueous solvent is selected from water;
wherein said nanoemulsion has a particles of particle size between 203 to 231 nm, and a zeta potential between −30 to −36 mV; and,
wherein the nanoemulsion composition is obtained by:
dissolving the curcumin in a miscible solvent selected from acetone, ethanol or combinations thereof;
encapsulating the curcumin in the oil core to produce an organic phase solution;
adding the stabilizer to the organic phase solution;
dispersing the organic phase solution in the aqueous solvent; and
evaporating the mixture until a volume of about 1 ml to about 10 ml remains,
whereby topical administration of the composition treats tumor reincidence, cancer relapse or metastasis after surgery in a subject in need thereof.

2. The nanoemulsion composition of claim 1, wherein the amount of the pharmaceutically acceptable oil added is about 400 µl to about 800 µl per 100 ml of the aqueous solvent.

3. The nanoemulsion composition of claim 2, wherein the amount of pharmaceutically acceptable oil added is about 500 µl to about 700 µl per 100 ml of the aqueous solvent.

4. The nanoemulsion composition of claim 1, wherein at least one dose of said nanoemulsion is applied to the subject in need thereof.

5. The nanoemulsion composition of claim 4, wherein said topical administration is applied to a body area after intervention by surgery for tumor excision.

6. The nanoemulsion composition of claim 5, wherein said subject is a mammal.

7. The nanoemulsion composition of claim 6, wherein said mammal is a human.

* * * * *